(12) United States Patent
Choudary et al.

(10) Patent No.: US 6,881,839 B2
(45) Date of Patent: Apr. 19, 2005

(54) PROCESS FOR PREPARING DILTIAZEM USING A HETEROGENEOUS TRIFUNCTIONAL CATALYST

(75) Inventors: Boyapati M. Choudary, Andhra Pradesh (IN); Naidu S. Chowdari, Andhra Pradesh (IN); Sateesh Madhi, Andhra (IN); Lakshmi K. Mannepalli, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 44 days.

(21) Appl. No.: 10/334,122

(22) Filed: Dec. 31, 2002

(65) Prior Publication Data

US 2004/0127704 A1 Jul. 1, 2004

(51) Int. Cl.$^7$ ............................................. C07D 281/10
(52) U.S. Cl. ....................................... 540/491
(58) Field of Search ......................... 540/491

(56) References Cited

PUBLICATIONS

Lohray et al, "Anchimeric Assisted Unprecedented Sni–type Cleavage of Cyclic Sulfite: Application in the Synthesis of The Calcium Channel Blocker Diltiazem", J. Org. Chem., vol. 60, 1995, pp. 5983–5985, XP002251356.

Choudary, "A Trifunctional Catalyst For the Synthesis of Chiral Diols", Angewandte, Chemie, International Edition, Verlag Chemie, Weinheim, DE, vol. 40, No. 24, Dec. 17, 2001, pp. 4620–4623, XP00111177, ISSN: 0570–0833.

*Primary Examiner*—Taofiq Solola
(74) *Attorney, Agent, or Firm*—Nixon & Vanderhye P.C.

(57) ABSTRACT

The present invention comprises a simplified synthesis of (+)-diltiazem through IE-PdOsW wherein IE is ion-exchanger, catalyzed three-component coupling reaction and $Fe^{3+}$-exchanged clay catalyzed ring opening of sulfite with 2-aminothiophenol followed by cyclization as key steps.

17 Claims, No Drawings

PROCESS FOR PREPARING DILTIAZEM USING A HETEROGENEOUS TRIFUNCTIONAL CATALYST

FIELD OF THE INVENTION

The present invention relates to an improved process for the preparation of diltiazem by first synthesizing (2R,3S)-(−)-Ethyl-2,3-dihydroxy-3-(4-methoxyphenyl)propionate with greater than 99% enantioselectivity and devoid of osmium even in a crude form in a single pot using recyclable multifunctional catalysts of the formula IE-IE-PdOsW, in which IE is a ion-exchanger comprising LDH, quaternary ammonium salt anchored on silica, clay, alumina, magnesia or resin, converting the diol obtained without further crystallization into cyclic sulfite and reacting the cyclic sulfite with 2-aminothiophenol in the presence of $Fe^{3+}$-exchanged clay in xylene to obtain a cyclic lactam which is then subjected to N-alkylation and acylation to provide diltiazem.

BACKGROUND OF THE INVENTION

Diltiazem, a typical calcium antagonist, has been used throughout the world as a remedy for angina and hypertension. Among the four possible stereoisomers of diltiazem, only the (+)-(2S,3S)-isomer exhibits potent coronary vasodilating activity. Therefore, diltiazem has been developed and marketed as a single isomer. For the synthesis of diltiazem, many processes have been extensively investigated and at present it is mainly manufactured by the route using the optically active (−)-trans methyl glycidate as a key intermediate, which is prepared via enzymatic methods. However, there is an inherent drawback to the optical resolution in that the maximum yield of one enantiomer cannot exceed 50%. Although several approaches for the asymmetric synthesis of diltiazem have been reported, for reasons involving enantiomeric purity and overall efficiency, a more efficient method is needed.

Reference is made to U.S. Pat. No. 5,869,697, (1999) wherein synthesis of diltiazem was carried out by using optically pure chiral diols. The inherent disadvantage is the optically pure diols used are expensive involving tedious experimental procedures. Reference is also made to U.S. Pat. No. 6,180,785 (2001) wherein synthesis of diltiazem was carried out by using optically pure chiral diols. The inherent disadvantage is the optically pure diols used are expensive, involving tedious experimental procedures.

Reference is made to J. Org. Chem. 1992, 57, 851 wherein optically active trans-phenylglycidic acid ester is prepared using chiral auxiliary followed by a stereoselective opening of the epoxide by various substituted aminothiophenols to give the desired intermediate ester for diltiazem. The inherent disadvantage is the use of stoichiometric amount of chiral auxiliary. Reference is also made to Tetrahedron Lett. 2001, 42, 1313 wherein optically active trans-phenylglycidic acid ester is prepared via chiral oxazaborolidine-mediated Mukaiyama aldol reaction followed by reduction and cyclization. The inherent disadvantage is the use of a stoichiometric amount of an expensive reagent.

Reference is made to J. Org. Chem., 1996, 61, 6730 wherein optically active diols were prepared via enantioselective lipase catalyzed hydrolysis of threo-diacetate ethyl ester which leads to (+)-diltiazem precursors (2S,3R)-diol and (2R,3S)-diol. The inherent disadvantage is the recovery of an entirely toxic osmium tetroxide to prepare threo-diol ester.

OBJECTS OF THE INVENTION

The main object of the invention is to provide a process for the preparation of diltiazem that comprises the following steps: (a) Synthesis of (2R,3S)-(−)-Ethyl-2,3-dihydroxy-3-(4-methoxyphenyl)propionate with greater than 99% enantioselectivity and devoid of osmium even in crude form in a single pot using recyclable multifunctional catalysts of the formula IE-IE-PdOsW, in which IE is a ion-exchanger comprising LDH, quaternary ammonium salt anchored on silica, clay, alumina, magnesia or resin (b) conversion of the diol thus obtained without further crystallization into cyclic sulfite using standard protocol, (c) cyclic sulfite on reaction with 2-aminothiophenol in the presence of $Fe^{3+}$-exchanged clay in xylene at 120–140° C. gave the cyclic lactam, (d) cyclic lactam was in turn subjected for N-alkylation, and acylation to afford diltiazem.

Another object of the invention is to provide a novel and ecofriendly process for synthesis of (2R,3S)-(−)-Ethyl-2,3-dihydroxy-3-(4-methoxyphenyl)propionate from 4-haloanisole and ethyl acrylate in a single pot using a multifunctional catalyst.

It is another object of the invention to provide a process for the synthesis of (2R,3S)-(−)-Ethyl-2,3-dihydroxy-3-(4-methoxyphenyl)propionate dispensing with the use of soluble and toxic osmium tetroxide or potassium osmate dihydrate.

It is another object of the invention to provide a process for the preparation of diltiazem wherein the enantioselectivity and yields obtained are higher than reported in homogeneous dihydroxylation.

It is another object of the invention to provide a process for the preparation of diltiazem wherein the work-up procedure is simple.

It is another object of the invention to provide a process for the preparation of diltiazem wherein the catalyst is capable of being recycled with consistent activity.

SUMMARY OF THE INVENTION

The present invention comprises a simplified synthesis of (+)-diltiazem through IE-PdOsW wherein IE is ion-exchanger, catalyzed three-component coupling reaction and $Fe^{3+}$-exchanged clay catalyzed ring opening of sulfite with 2-aminothiophenol followed by cyclization as key steps.

The IE-PdOsW catalyzes the one pot synthesis of optically pure diol starting from 4-iodoanisole and ethyl acrylate using $H_2O_2$ as a terminal oxidant. The diol was converted to the corresponding sulfite and upon reaction with 2-aminothiophenol in the presence of $Fe^{3+}$-exchanged clay in xylene at 120–140° C. gave the cyclic lactam. N-alkylation, followed by acylation of lactam gave the diltiazem in 37% overall yield. It is significant to note that $Fe^{3+}$-exchanged clay was used for this purpose as a new variant to the conventional acid catalysts to obtain quantitative yields.

Accordingly the present invention provides an improved process for preparing diltiazem comprising (a) synthesizing (2R,3S)-(−)-Ethyl-2,3-dihydroxy-3-(4-methoxyphenyl)propionate using a recyclable multifunctional catalyst of the formula IE-PdOsW wherein IE is an ion exchanger to obtain a diol, (b) converting the diol obtained without further crystallization into cyclic sulfite, (c) reacting the cyclic sulfite 2-aminothiophenol in the presence of $Fe^{3+}$-exchanged clay in xylene to obtain the corresponding cyclic lactam, (d) subjecting the cyclic lactam obtained to N-alkylation and acylation to obtain diltiazem.

In one embodiment of the invention, in step (a) (2R,3S)-(−)-Ethyl-2,3-dihydroxy-3-(4-methoxyphenyl)propionate is synthesized with greater than 99% enantioselectivity and devoid of osmium even in crude form.

In another embodiment of the invention, the ion exchanger is selected from the group consisting of LDH, a quaternary ammonium salt anchored on silica, clay, alumina and magnesia, and resin.

In yet another embodiment of the invention, the catalyst is selected from the group consisting of LDH-PdOsW, resin-PdOsW and $SiO_2$—PdOsW.

In another embodiment of the invention, the diol is converted to the cyclic sulfite by dissolving it in pyridine and reacting with thionyl sulfide In a further embodiment of the invention, in step (c) cyclic sulfite is reacted with 2-aminothiophenol in the presence of $Fe^{3+}$-exchanged clay in xylene at a temperature in the range of 120–140° C.

In another embodiment of the invention, the active species in the catalyst ranges between 5 to 30%.

In another embodiment of the invention, the multifunctional catalyst used in the reaction comprises 0.01 to 10 mol % of active species with respect to the substrate.

In another embodiment of the invention, the multifunctional catalyst is recovered by filtration and reused for several cycles with consistent activity.

In another embodiment of the invention, (2R,3S)-(−)-Ethyl-2,3-dihydroxy-3-(4-methoxyphenyl)propionate is synthesized using a recyclable multifunctional catalyst of the formula IE-PdOsW wherein IE is a ion-exchanger selected from the group consisting of LDH, quaternary ammonium salt anchored on silica, clay, alumina and magnesia, and resin, in catalytic amounts to provide the desired prochiral olefins and NMO in situ, by Heck coupling of ethyl acrylate and 4-haloanisole, and N-oxidation of an amine with hydrogen peroxide, for asymmetric dihydroxylation in the presence of a cinchona alkaloid compound and in a solvent to provide a pure vicinal diol.

In another embodiment of the invention, the 4-haloanisole comprises 4-iodoanisole.

In another embodiment of the invention, the reaction in step (a) is carried out using a solvent selected from the group consisting of water, acetone, acetonitrile and t-butanol.

In another embodiment of the invention, N-oxidation is carried out using an amine selected from the group consisting of N-methyl morpholine (NMM), trimethyamine and triethylamine.

In another embodiment of the invention, the cinchona alkaloid comprises a chiral ligand selected from the group consisting of $(DHQ)_2PHAL$, $(DHQD)_2PYR$, $(DHQD)_2AQN$, DHQD-OAc, DHQD-CLB, DHQD-PHN, DHQD-MEQ, DHQD-IND and pseudoenantiomeric forms thereof.

In another embodiment of the invention, Heck coupling reaction and N-oxidation are effected at a temperature in the range −20 to +200° C. and for a time period in the range of 0.5 to 48 h.

In another embodiment of the invention, Heck coupling is carried out using a base selected from the group consisting of triethylamine, tributylamine, potassium fluoride and potassium acetate.

The present invention also provides a process for the preparation of diltiazem comprising synthesizing (2R,3S)-(−)-Ethyl-2,3-dihydroxy-3-(4-methoxyphenyl)propionate is synthesized using a recyclable multifunctional catalyst of the formula IE-PdOsW wherein IE is a ion-exchanger selected from the group consisting of LDH, quaternary ammonium salt anchored on silica, clay, alumina and magnesia, and resin, in catalytic amounts to provide the desired prochiral olefins and NMO in situ, by Heck coupling of ethyl acrylate and 4-haloanisole, and N-oxidation of an amine selected from the group consisting of N-methyl morpholine (NMM), trimethyamine and triethylamine with hydrogen peroxide, for the asymmetric dihydroxylation in the presence of a cinchona alkaloid compound and in a solvent selected from the group consisting of water, acetone, acetonitrile and t-butanol at a temperature in the range of −20 to +200° C. for a period 0.5 to 48 h, to provide a pure vicinal diol, (b) converting the diol obtained without further crystallization into cyclic sulfite, (c) reacting the cyclic sulfite 2-aminothiophenol in the presence of $Fe^{3+}$-exchanged clay in xylene to obtain the corresponding cyclic lactam, (d) subjecting the cyclic lactam obtained to N-alkylation and acylation to obtain diltiazem.

DETAILED DESCRIPTION OF THE PRESENT INVENTION

The novelty of the present invention lies in the preparation of diltiazem by the synthesis of (2R,3S)-(−)-Ethyl-2,3-dihydroxy-3-(4-methoxyphenyl)propionate with greater than 99% enantioselectivity and devoid of osmium even in crude in a single pot using a recyclable multifunctional catalyst of the formula IE-PdOsW, and conversion of diol thus obtained without further crystallization into cyclic sulfite using standard protocol, which upon on reaction with 2-aminothiophenol in the presence of $Fe^{3+}$-exchanged clay in xylene at 120–140° C. gave the cyclic lactam, which was in turn subjected to N-alkylation, and acylation as described in Scheme 1. Higher yields and enantioselectivities are obtained when multifunctional catalysts are used in synthesis of (2R,3S)-(−)-Ethyl-2,3-dihydroxy-3-(4-methoxyphenyl)propionate The consistent activity and enantioselectivity obtained for several cycles in multicomponent reaction makes the process economical and possible for commercial realization. Thus, this invention offers the best techno-economic route for the synthesis of (2R,3S)-(−)-Ethyl-2,3-dihydroxy-3-(4-methoxyphenyl)propionate.

Scientific Explanation:

The present invention provides an improved process for the preparation of diltiazem that comprises the following steps: (a) Synthesis of (2R,3S)-(−)-Ethyl-2,3-dihydrOxy-3-(4-methoxyphenyl)propionate with greater than 99% enantioselectivity and devoid of osmium even in crude form in a single pot using recyclable multifunctional catalysts of the formula IE-IE-PdOsW, in which IE is a ion-exchanger comprising LDH, quaternary ammonium salt anchored on silica, clay, alumina, magnesia or resin (b) conversion of the diol thus obtained without further crystallization into cyclic sulfite using standard protocol, (c) cyclic sulfite on reaction with 2-aminothiophenol in the presence of $Fe^{3+}$-exchanged clay in xylene at 120–1400C. gave the cyclic lactam, (d) cyclic lactam was in turn subjected to N-alkylation, and acylation to yield diltiazem.

(2R,3S)-(−)-Ethyl-2,3-dihydroxy-3-(4-methoxyphenyl) propionate which is the important intermediate for diltiazem was synthesized using multifunctional catalysts in catalytic amount by tandem and/or simultaneous reactions involving Heck coupling, N-oxidation and asymmetric dihydroxylation of olefins employing hydrogen peroxide as terminal oxidant in presence of cinchona alkaloid compounds in a heterogeneous way.

The following examples are given by way of illustration and therefore should not be construed to limit the scope of the invention.

EXAMPLE 1

Preparation of Trifunctional Catalysts a) Preparation of LDH-PdOsW 1 g of LDH was suspended in 100 mL of aqueous solution containing $Na_2PdCl_4$, $K_2OsO_4.2H_2O$ and $Na_2WO_4.2H_2O$ (0.3 mmol each) and stirred at 25° C. for 12 h under nitrogen atmosphere. The solid catalyst was filtered, washed thoroughly with 500 mL of water and vacuum dried to obtain 1.181 g of LDH-PdOsW (0.25 mmol $g^{-1}$ each of Pd, Os and W).

b) Preparation of Resin-PdOsW

Resin was obtained by quaternization of triethylamine (2.1 mL, 21 mmol) with 1 g of chloromethylated styrene-divinylbenzene copolymer (Merrifield resin, capacity ~2.1 mequiv/g) in chloroform (20 mL) under reflux for 24 h. 1 g of quaternary ammonium resin was suspended in 100 mL of aqueous solution containing $Na_2PdCl_4$, $K_2OsO_4.2H_2O$ and $Na_2WO_4.2H_2O$ (0.25 mmol each) and stirred at 25° C. for 12 h under nitrogen atmosphere. The solid catalyst was filtered, washed thoroughly with 500 mL of water and vacuum dried to obtain resin-PdOsW (0.2 mmol $g^{-1}$ of each Pd, Os and W).

c) Preparation of $SiO_2$—PdOsW

Modified silica was obtained by quaternisation of triethylamine (0.7 mL, 7 mmol) with bromopropylsilica (capacity 0.7 mequiv/g) in chloroform (20 mL) under reflux for 24 h. 1 g of quaternary ammonium silica was suspended in 100 mL of aqueous solution containing $Na_2PdCl_4$, $K_2OsO_4.2H_2O$ and $Na_2WO_4.2H_2O$ (0.11 mmol each) and stirred at 25° C. for 12 h under nitrogen atmosphere. The solid catalyst was filtered, washed thoroughly with 500 mL of water and vacuum dried to obtain $SiO_2$—PdOsW (0.1 mmol $g^{-1}$ of each Pd, Os and W).

d) $Fe^{3+}$-exchanged montmorillonite catalyst: To a 1 lt. stirred aqueous solution of $FeCl_3.6H_2O$ (1.0 M), 80 g of K10-montmorillonite was added. Stirring was maintained for 16–30 hrs in order to saturate the exchange capacity of K10 montmorillonite. The clay suspension was centrifuged and the supernatant solution was discarded.

Washing cycles were repeated until disappearance of $Cl^-$ ions from the discarded water. The clay was dried overnight in an oven at 120° C. and finely ground in a mortar.

EXAMPLE 2

Experimental Procedure for the Synthesis of Diltiazem a) Synthesis of (2R,3S)-(−)-Ethyl-2,3-dihydroxy-3-(4-methoxyphenyl)propionate LDH-PdOsW (0.4 g, 0.1 mmol), 4-iodoanisole (10 mmol), ethyl acrylate (10 mmol) and $Et_3N$ (11 mmol) were stirred at 70° C. for 16 h under nitrogen atmosphere. After completion of the Heck coupling, the heating was stopped and the reaction was allowed to reach room temperature. A mixture of $(DHQ)_2PHAL$ (7.8 mg, 0.1 mmol) and NMM (0.5 g, 5 mmol) in BuOH—$H_2O$ (5:1, 50 mL) was added in one portion to the reaction flask under stirring. $H_2O_2$ (30% aqueous, 15 mmol) was then slowly added over 15 h using a syringe pump. After the addition was complete, the stirring was continued for an additional 1 h and the catalyst was filtered and washed with ethyl acetate (100 mL). After removal of the solvent, thus obtained crude material was chromatographed on silica gel using hexane/ethyl acetate (1:1) as eluant to afford ethyl (2R,3S)-2,3-dihydroxy-3-(4-methoxyphenyl)propionate (92% yield).

b) Preparation of 4(S)-(P-methoxyphenyl)-5(R)-(carboxyethyl)-1,3-dioxathiolane 2-oxide The diol (1.2 mmol) was dissolved in dry pyridine (2 mL) under argon. The reaction mixture was cooled to 0° C. and freshly distilled thionyl chloride (1.3 mmol) was added drop wise. The reaction mixture was stirred at 0° C. for 2 h and poured onto crushed ice containing dilute HCl. The reaction mixture was extracted with ether, washed with dilute HCl, aqueous $NaHCO_3$ and brine and dried ($Na_2SO_4$) evaporated under reduced pressure to give a pale yellow oil which was chromatographed over silica gel to furnish 4(S)-(p-methoxyphenyl)-5-(R)-(carboxyethyl)-1,3-dioxathiolane 2-oxide (98% yield).

c) Preparation of Hydroxy Lactam

A flame-dried two-necked 25 mL round-bottomed flask was charged with cyclic sulfite (1 mmol), $Fe^{3+}$-clay (100 mg) and dry xylene (5 mL) and stirred under a constant flush of nitrogen. Freshly distilled 2-aminothiophenol (0.9 mmol) was added drop wise, and the reaction mixture was refluxed for 12 h. Crude compound was chromatographed to get cis-(+)-2,3-dihydro-3-hydroxy-2-(4-methoxyphenyl)-1,5-benzothiazepin-4(5H)-one (50% yield). The hydroxy lactam (0.54 mmol) was dissolved in ethyl acetate (5 mL) and 2-(dimethylamino) ethyl chloride hydrochloride (0.694 mmol) was added followed by addition of finely ground $K_2CO_3$ (2.16 mmol) and a drop of water. The heterogeneous mixture was stirred at reflux for 12 h. Solvent was removed and the crude product was chromatographed to obtain N-alkylated product (88%).

d) Preparation of Cis-(+)-3-(Acetyloxy)-2,3-dihydo-5-[2-(dimethylamino)-ethyl]-2-(4-methoxyphenyl)-1,5-benzothiazepin-4(5H)-one Hydrochloride (Diltiazem Hydrochloride)

The N-alkylated lactam (0.317 mmol), $Ac_2O$ (1 mmol), $Et_3N$ (2 mmol) and DMAP (0.03 mmol) taken in $CH_2Cl_2$ (5 mL) were heated at reflux under $N_2$ for 3 h. The mixture was poured into ice water and brine was added. The organic layer was separated and the aqueous layer was extracted with $CH_2Cl_2$ (10 mL). The combined organic layers were washed with 5% $NH_4OH$ (5 mL) solution, dried ($Na_2SO_4$) and evaporated. The residue was dissolved in MeOH (2 mL) and treated with anhydrous HCl gas till pH was 2. Ether (3 mL) was added to the resulting solution. The precipitated solids were collected by filtration and washed with 10% MeOH-ether to afford diltiazem hydrochloride (92% yield).

The invention is further explained by reference Scheme 1 which illustrates the present reaction schemes in the production of diltiazem.

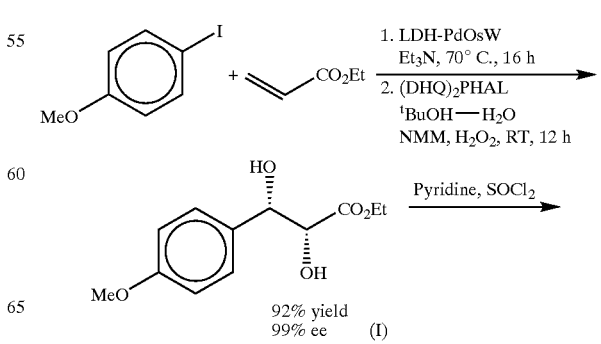

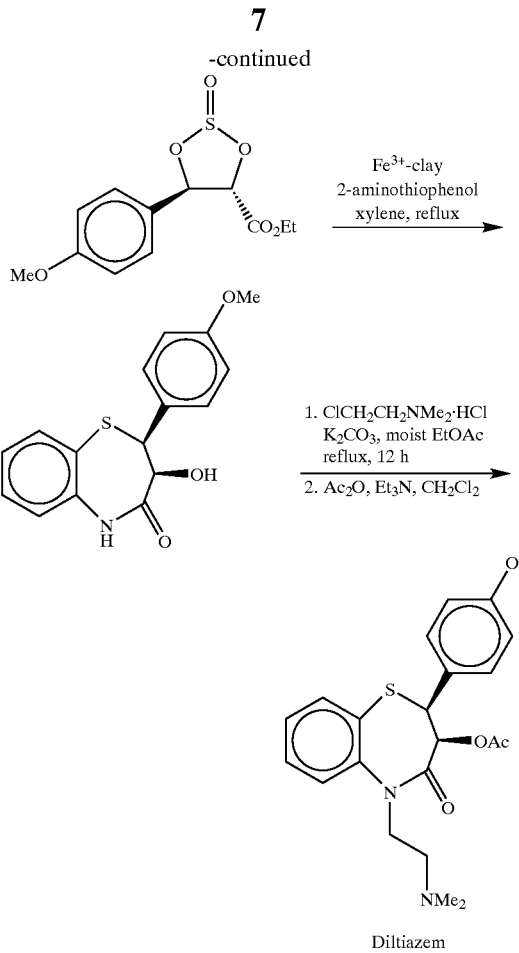

The Main Advantages of the Present Invention are:
1. A novel and ecofriendly process for the synthesis of diltiazem starting from aryl halides and olefins using heterogeneous multifunctional catalyst is presented.
2. The present process dispenses the use of soluble, toxic osmium tetraoxide or potassium osmate dihydrate and instead we used heterogeneous reusable multifunctional catalysts to prepare (2R,3S)-(−)-Ethyl-2,3-dihydroxy-3-(4-methoxyphenyl)propionate. This catalyst is important in the sense that they are useful in catalyzing three different reactions by generating the precursors, prochiral olefins and NMO for AD reaction in situ from the readily available cheaper starting materials such as ethyl acrylate and 4-haloanisole and hence saves the energy and time, which are vital for a better and economical process.
3. Multifunctional catalysts are prepared and used as heterogeneous catalysts for synthesis of (2R,3S)-(−)-Ethyl-2,3-dihydroxy-3-(4-methoxyphenyl)propionate chiral diols. Use of heterogeneous multifunctional catalysts precludes the presence of osmium in the product.
4. The (2R,3S)-(−)-Ethyl-2,3-dihydroxy-3-(4-methoxyphenyl)propionate obtained using heterogeneous multifunctional catalyst was put to direct use in the synthesis of ditiazem without any further crystallization.
5. Reusable $Fe^{3+}$-clay is used to prepare hydroxy lactam.
6. The enantioselectivity and the yields obtained are higher than reported in homogeneous dihydroxylation.
7. The work-up procedure is simple.
8. The catalyst is subjected to many recycles, which displayed consistent activity.
9. The present process is environmentally safe since there is no disposal problem.
10. The process is economical.

We claim:
1. A process for preparing diltiazem comprising:
   (a) preparing a diol by synthesizing (2R,3S)-(−)-Ethyl-2,3-dihydroxy-3-(4-methoxyphenyl)propionate using a recyclable multifunctional catalyst of the formula IE-PdOsW wherein IE is an ion exchanger, wherein the synthesis comprises tandem or simultaneous Heck coupling of ethyl acrylate and 4-haloanisole, and N-oxidation of an amine using hydrogen peroxide, for asymmetric dihydroxylation in the presence of a cinchona alkaloid compound and in a solvent,
   (b) converting the diol without further crystallization into a cyclic sulfite by dissolving the diol in a solvent and reacting with thionyl chloride,
   (c) reacting the cyclic sulfite 2-aminothiophenol in the presence of $Fe^{3+}$-exchanged clay in xylene to obtain a corresponding cyclic lactam,
   (d) subjecting the cyclic lactam to N-alkylation and acylation to obtain diltiazem.
2. A process as claimed in claim 1 wherein in step (a) the (2R,3S)-(−)-Ethyl-2,3-dihydroxy-3-(4-methoxyphenyl)propionate is synthesized with greater than 99% enantioselectivity and is devoid of osmium even in crude form.
3. A process as claimed in claim 1 wherein the ion exchanger is selected from the group consisting of LDH, quaternary ammonium salt anchored on silica, clay, alumina and magnesia, and resin.
4. A process as claimed in claim 1 wherein the multifunctional catalyst is selected from the group consisting of LDH-PdOsW, resin-PdOsW and $SiO_2$—PdOsW.
5. A process as claimed in claim 1 wherein step (c) is carried out at a temperature in the range of 120–140° C.
6. A process as claimed in claim 1 wherein the multifunctional catalyst comprises an active species in the range of 5 to 30%.
7. A process as claimed in claim 1 wherein the multifunctional catalyst comprises 0.01 to 10 mol % of active species with respect to a substrate.
8. A process as claimed in claim 1 wherein the multifunctional catalyst is recovered by filtration and reused.
9. A process as claimed in claim 1 wherein the solvent used in step (a) is selected from the group consisting of water, acetone, acetonitrile and t-butanol.
10. A process as claimed in claim 1 wherein the amine used in step (a) is selected from the group consisting of N-methyl morpholine, trimethylamine and triethylamine.
11. A process as claimed in claim 1 wherein step (a) comprises the synthesis of (2R,3S)-(−)-Ethyl-2,3-dihydroxy-3-(4-methoxyphenyl)propionate using a catalytic amount of a recyclable multifunctional catalyst of the formula IE-PdOsW wherein IE is an ion-exchanger selected from the group consisting of LDH, quaternary ammonium salt anchored on silica, clay, alumina and magnesia, and resin, to obtain desired prochiral olefins and NMO in situ, by Heck coupling of ethyl acrylate and 4-haloanisole, and N-oxidation of an amine with hydrogen peroxide, for asymmetric dihydroxylation in the presence of a cinchona alkaloid compound and in a solvent to provide a pure vicinal diol.
12. A process as claimed in claim 11 wherein the 4-haloanisole comprises 4-iodoanisole.
13. A process as claimed in claim 11 wherein in step (a) the solvent is selected from the group consisting of water, acetone, acetonitrile and t-butanol.
14. A process as claimed in claim 11 wherein the N-oxidation is carried out using an amine selected from the group consisting of N-methyl morpholine (NNM), trimethylamine and triethylamine.

15. A process as claimed in claim 11 wherein the cinchona alkaloid is a chiral ligand selected from the group consisting of (DHQ)$_2$PHAL, (DHQD)$_2$PYR, (DHQD)$_2$AQN, DHQD-OAc, DHQD-CLB, DHQD-PHN, DHQD-MEQ, DHQD-IND and pseudoenantiomeric forms thereof.

16. A process as claimed in claim 11 wherein the Heck coupling reaction and N-oxidation are effected at a temperature in the range −20 to +200° C. and for a time period in the range of 0.5 to 48 hours and wherein the Heck coupling is carried out using a base selected from the group consisting of triethylamine, tributylamine, potassium fluoride and potassium acetate.

17. A process for the preparation of diltiazem comprising:
   (a) preparing a pure vicinal diol by synthesizing (2R,3S)-(−)-Ethyl-2,3-dihydroxy-3-(4-methoxyphenyl) propionate using a catalytic amount of a recyclable multifunctional catalyst of the formula IE-PdOsW wherein IE is a ion-exchanger selected from the group consisting of LDH, quaternary ammonium salt anchored on silica, clay, alumina and magnesia, and resin to obtain desired prochiral olefins and NMO in situ, the synthesis comprising tandem or simultaneous Heck coupling of ethyl acrylate and 4-haloanisole, and N-oxidation of an amine selected from the group consisting of N-methyl morpholine (NMM), trimethylamine and triethylamine with hydrogen peroxide for asymmetric dihydroxylation in the presence of a cinchona alkaloid compound and in a solvent selected from the group consisting of water, acetone, acetonitrile and t-butanol at a temperature in the range of −20 to +200° C. for a period 0.5 to 48 hours,
   (b) converting the diol without further crystallization into a cyclic sulfite by dissolving the diol in a solvent and reacting with thionyl chloride,
   (c) reacting the cyclic sulfite with 2-aminothiophenol in the presence of $Fe^{3+}$-exchanged clay in xylene to obtain a corresponding cyclic lactam,
   (d) subjecting the cyclic lactam to N-alkylation and acylation to obtain diltiazem.

* * * * *